United States Patent
Han et al.

(10) Patent No.: US 12,351,595 B2
(45) Date of Patent: Jul. 8, 2025

(54) COMPOSITION COMPRISING O-CYCLIC PHYTOSPHINGOSINE-1-PHOSPHATE FOR PREVENTING OR TREATING PARKINSON'S DISEASE

(71) Applicant: AXCESO BIOPHARMA CO., LTD., Anyang-si (KR)

(72) Inventors: Won Kyo Han, Gwangju-si (KR); Young Jun Park, Yongin-si (KR); Myeong Jun Choi, Seoul (KR)

(73) Assignee: AXCESO BIOPHARMA CO., LTD., Anyang-si (KR)

( * ) Notice: Subject to any disclaimer, the term of this patent is extended or adjusted under 35 U.S.C. 154(b) by 772 days.

(21) Appl. No.: 17/625,487

(22) PCT Filed: Jul. 9, 2020

(86) PCT No.: PCT/KR2020/009015
§ 371 (c)(1),
(2) Date: Jan. 7, 2022

(87) PCT Pub. No.: WO2021/006663
PCT Pub. Date: Jan. 14, 2021

(65) Prior Publication Data
US 2022/0289777 A1    Sep. 15, 2022

(30) Foreign Application Priority Data
Jul. 11, 2019  (KR) .................... 10-2019-0083866

(51) Int. Cl.
*C07F 9/6574*  (2006.01)
*A61P 25/16*   (2006.01)

(52) U.S. Cl.
CPC .......... *C07F 9/65742* (2013.01); *A61P 25/16* (2018.01)

(58) Field of Classification Search
CPC ............................. C07F 9/65742; A61P 25/16
See application file for complete search history.

(56) References Cited

FOREIGN PATENT DOCUMENTS

| | | |
|---|---|---|
| CN | 105246903 A | 1/2016 |
| EP | 3 501 524 A1 | 6/2019 |
| EP | 3 502 237 A1 | 6/2019 |
| KR | 10-1003532 B1 | 12/2010 |
| KR | 10-2011-0020073 A | 3/2011 |
| KR | 10-2012-0023302 A | 3/2012 |
| KR | 10-1340556 B1 | 12/2013 |
| KR | 10-1514970 B1 | 4/2015 |
| KR | 10-2016-0000969 A | 1/2016 |
| KR | 10-2016-0146689 A | 12/2016 |
| KR | 10-2017-0138705 A | 12/2017 |
| KR | 10-1842438 B1 | 5/2018 |
| WO | WO-2007048034 A2 * | 4/2007 ............. A61K 31/57 |

OTHER PUBLICATIONS

English Translation of KR10182438 (Year: 2018).*
English Translation of KR101340556 (Year: 2013).*
English Translation of KR101514970 (Year: 2015).*
Lee et al, O-Cyclic Phytosphingosine-1-Phosphate Protects Against Motor Dysfunctions and Glial Cell Mediated Neuroinflammation in the Parkinson's Disease Mouse Models, Antioxidants, 2022, 11, 2017 (Year: 2022).*
International Search Report of PCT/KR2020/009015 dated Oct. 15, 2020 [PCT/ISA/210].
Zhang et al., "Morin exerts neuroprotective actions in Parkinson disease models in vitro and in vivo", Acta Pharmacologica Sinica, vol. 31, No. 8, Jul. 19, 2010, pp. 900-906.
Tansey et al., "Immune system responses in Parkinson's disease: Early and dynamic", Eur J Neurosci., vol. 49, No. 3, Dec. 10, 2018, pp. 364-383.
Miho Murata, "Discovery of new anti-Parkinson's drug zonisamide", Clinical Neurology, vol. 50, No. 2, 2010, pp. 67-73.
Extended European Search Report dated Jun. 30, 2023 in application No. 20836166.7.
Communication issued Aug. 1, 2023 in Japanese Application No. 2022-500946.
Communication issued Nov. 22, 2022 in Japanese application No. 2022-500946.
Communication issued Nov. 23, 2023 in Chinese Application No. 202080049861.2.

* cited by examiner

*Primary Examiner* — Noble E Jarrell
*Assistant Examiner* — Phillip Matthew Rzeczycki
(74) *Attorney, Agent, or Firm* — Sughrue Mion, PLLC

(57) ABSTRACT

A pharmaceutical or health food composition for preventing or treating Parkinson's disease containing O-cyclic phytosphingosine-1-phosphate. The composition can prevent the death of SH-SY5Y nerve cells, which are dopaminergic nerve cells, and increase the expression of tyrosine hydroxylase, an enzyme required for dopamine formation. Accordingly, the composition can be effectively used for preventing or treating Parkinson's disease.

6 Claims, 2 Drawing Sheets

[Fig. 1]
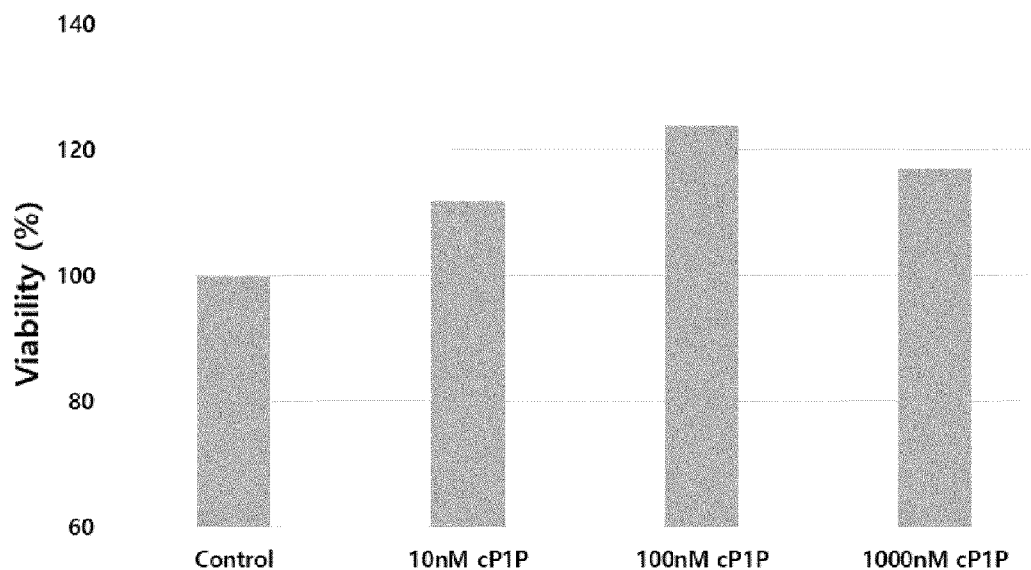
[Fig. 2]
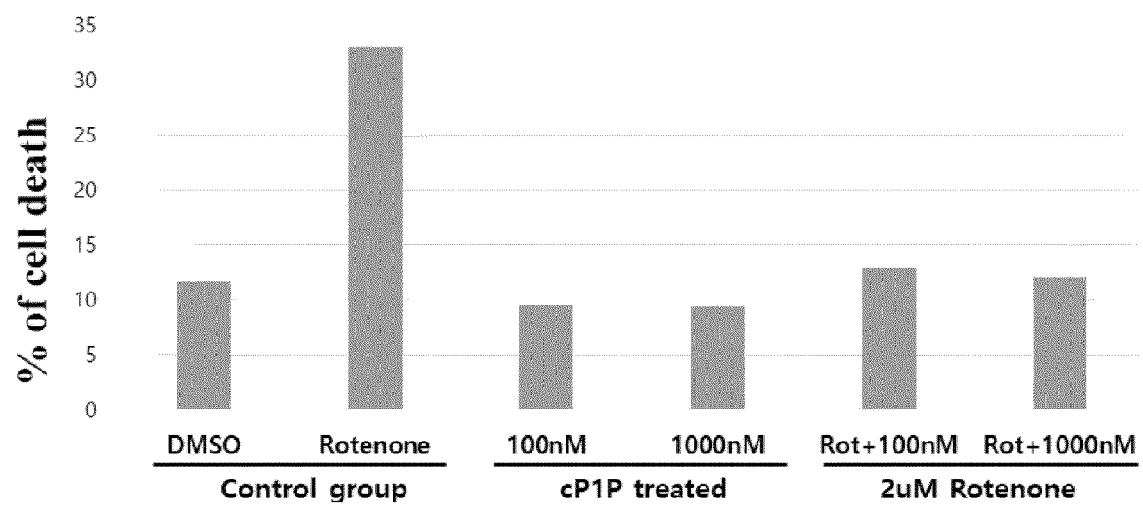

[Fig. 3]
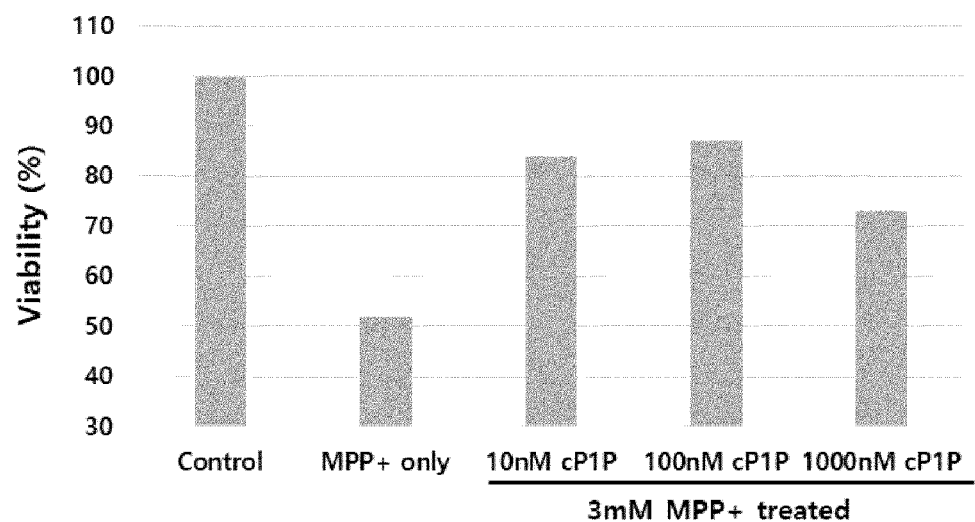
[Fig. 4]
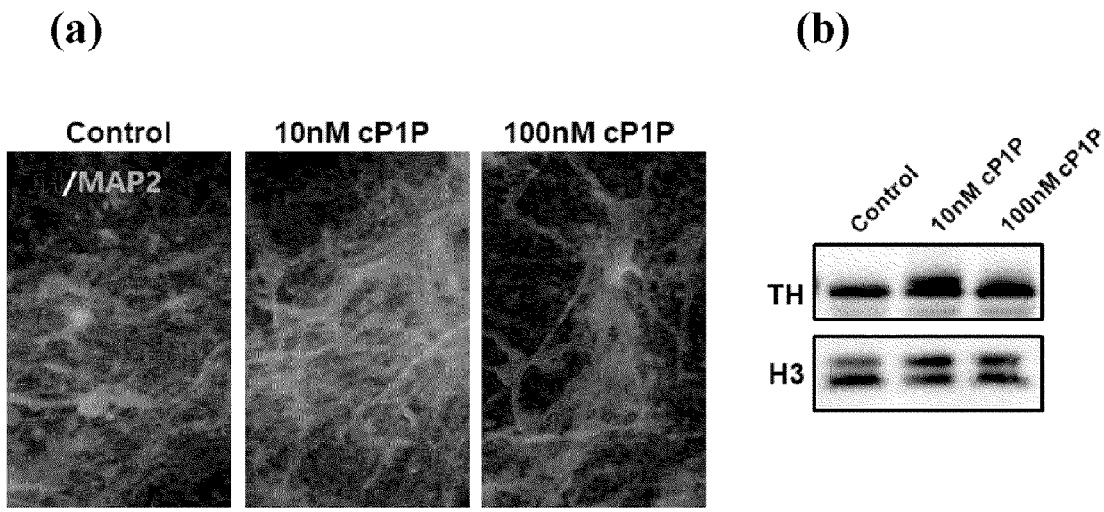

COMPOSITION COMPRISING O-CYCLIC PHYTOSPHINGOSINE-1-PHOSPHATE FOR PREVENTING OR TREATING PARKINSON'S DISEASE

CROSS REFERENCE TO RELATED APPLICATIONS

This application is a National Stage of International Application No. PCT/KR2020/009015, filed Jul. 9, 2020, claiming priority to Korean Patent Application No. 10-2019-0083866, filed Jul. 11, 2019.

TECHNICAL FIELD

The present disclosure relates to a composition for preventing or treating Parkinson's disease comprising O-cyclic phytosphingosine-1-phosphate. In particular, the present disclosure relates to a composition comprising O-cyclic phytosphingosine-1-phosphate which can inhibit the death of dopaminergic nerve cells and increase the expression of tyrosine hydroxylase, thereby preventing or treating Parkinson's disease.

BACKGROUND ART

Parkinson's disease (PD) is a disease caused by a deficiency of a neurotransmitter called dopamine. The deficiency of dopamine is caused by the gradual and selective loss of dopaminergic nerve cells in the substantia nigra region of the midbrain. Parkinson's disease causes tremor or paralysis of arms, legs, and face, stiffness, movement disorders due to bradykinesia and postural instability.

The causes of Parkinson's disease are very diverse. About 5% of all patients are caused by genetic factors, and external environmental factors such as inflammation and oxidative stress play an important role. Parkinson's disease is caused by abnormal aggregation of alpha-synuclein proteins in dopaminergic nerve cells. Aggregation of these proteins is further promoted by oxidative stress. So far, the treatment of Parkinson's disease has been achieved by supplementing dopamine neurotransmitters, but this does not provide a fundamental treatment for Parkinson's disease. For the fundamental treatment of Parkinson's disease, it is necessary to inhibit the death of nerve cells involved in the production of dopamine and to promote the production of dopamine. For the fundamental treatment of Parkinson's disease, researches on small molecule therapeutic drugs that directly target disease-modifying genes, gene therapy, monoclonal antibodies, immunotherapy targeting related indications, and biologics such as stem cells and induced pluripotent stem cells are ongoing. Recently, PD treatment using stem cells has been tried in clinical practice.

O-cyclic phytosphingosine-1-phosphate is a compound represented by the following Chemical Formula I, which has been disclosed in Korean Patent No. 10-1340556 as useful for preventing hair loss or promoting hair growth.

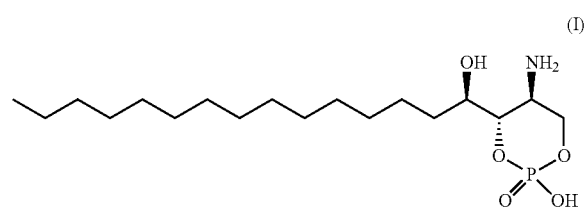

(I)

However, to date, no literature has been reported showing that O-cyclic phytosphingosine-1-phosphate can inhibit the death of SH-SY5Y nerve cells, which are dopaminergic nerve cells, and increase the expression of tyrosine hydroxylase, an enzyme required for dopamine formation, in a cell model of Parkinson's disease.

DISCLOSURE

Technical Problem

The present inventors have studied intensively to develop an effective therapeutic agent for Parkinson's disease, and as a result, found out that O-cyclic phytosphingosine-1-phosphate inhibits the death of SH-SY5Y nerve cells, which are dopaminergic nerve cells, and increases the expression of tyrosine hydroxylase, an enzyme required for dopamine formation, and completed the present invention.

Therefore, an object of the present disclosure is to provide a composition for preventing or treating Parkinson's disease comprising O-cyclic phytosphingosine-1-phosphate.

Technical Solution

One embodiment of the present disclosure relates to a pharmaceutical composition for preventing or treating Parkinson's disease comprising a compound represented by the following Chemical Formula I or a pharmaceutically acceptable salt thereof:

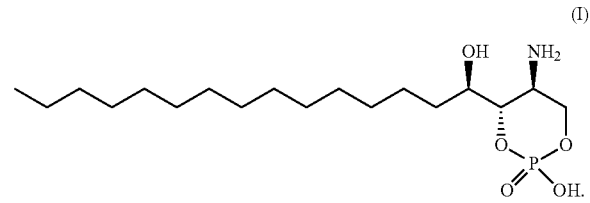

(I)

As used herein, the pharmaceutically acceptable salt includes both non-toxic inorganic and organic acid salts, for example, hydrochloride, sulfate, nitrate, phosphate, acetate, adipate, aspartate, benzoate, benzenesulfonate, citrate, camphorate, camphorsulfonate, diphosphate, ethanesulfonate, fumarate, glutamate, malate, lactate, methanesulfonate, succinate, tartrate, picrate, tosylate, and the like, and in particular, may be hydrochloride.

The compound represented by the Chemical Formula I or a pharmaceutically acceptable salt thereof can be obtained commercially or can be easily prepared by a method known in the art (refer to Korean Patent No. 10-1340556).

The compound represented by the Chemical Formula I of the present disclosure, or a pharmaceutically acceptable salt thereof was shown to inhibit nerve cell death in Parkinson's disease cell models induced by treatment with rotenone and MPP$^+$, respectively, in SH-SY5Y nerve cells, which are dopaminergic nerve cells, and increase the expression of tyrosine hydroxylase, an enzyme required for dopamine formation in nerve cells (Examples 2 to 4, FIGS. 2 to 4). Thus, the compound represented by the Chemical Formula I of the present disclosure, or a pharmaceutically acceptable salt thereof can be effectively used in a pharmaceutical composition for preventing or treating Parkinson's disease.

The pharmaceutical composition according to the present disclosure may comprise another therapeutic agent for Parkinson's disease in addition to the compound represented by the Chemical Formula I or a pharmaceutically acceptable salt thereof.

The pharmaceutical composition according to the present disclosure may be administered orally (e.g., ingestion or inhalation) or parenterally (e.g., injection, transdermal absorption, rectal administration), and the injection may be, for example, intravenous injection, subcutaneous injection, intramuscular injection or intraperitoneal injection. The pharmaceutical composition according to the present disclosure can be formulated as a tablet, capsule, granule, fine subtilae, powder, sublingual tablet, suppository, ointment, injection, emulsion, suspension, syrup, spray, etc., depending on the route of administration. Preferably, the pharmaceutical composition may be in the form of a tablet. The various types of the pharmaceutical composition according to the present disclosure can be prepared by known techniques using a pharmaceutically acceptable carrier commonly used for each formulation. Examples of the pharmaceutically acceptable carrier include excipients, binders, disintegrating agents, lubricants, preservatives, antioxidants, isotonic agents, buffers, coating agents, sweetening agents, solubilizing agents, bases, dispersing agents, wetting agents, suspending agents, stabilizing agents, coloring agents, and the like.

The pharmaceutical composition according to the present disclosure may contain the compound represented by the Chemical Formula 1 or a pharmaceutically acceptable salt thereof in an amount of about 0.001 to 95% by weight depending on the form thereof.

The specific dosage of the pharmaceutical composition of the present disclosure may vary depending on the type of the mammal including a human being treated, weight, gender, severity of disease, the judgment of a doctor, etc. Preferably, in the case of oral administration, 0.01 to 50 mg of the active ingredient per 1 kg of body weight may be administered, and in the case of parenteral administration, 0.01 to 10 mg of the active ingredient per 1 kg of body weight may be administered. The total daily dose may be administered at one time or divided into several doses depending on the severity of the disease, the judgment of the doctor, and the like.

One embodiment of the present disclosure relates to a health functional food for preventing or improving Parkinson's disease comprising a compound represented by the following Chemical Formula I or a pharmaceutically acceptable salt thereof:

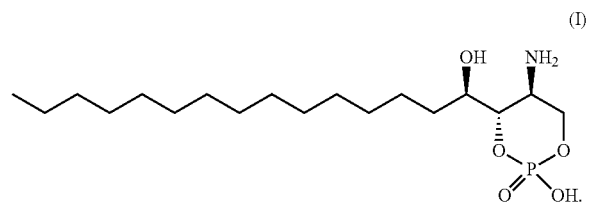

(I)

The type of the health functional food according to the present disclosure is not particularly limited, and it may be in the form of oral preparations such as powders, granules, tablets, capsules, suspensions, emulsions, syrups, or may be added to general foods such as candy, confectionery, gum, ice cream, noodle, bread, beverage, etc.

The health functional food of the present disclosure may be prepared using fillers, extenders, binders, wetting agents, disintegrants, sweeteners, fragrances, preservatives, surfactants, lubricants, excipients, and the like in a conventional manner depending on the form thereof.

In the preparation of the health functional food, the content of the compound represented by the Chemical Formula I or a pharmaceutically acceptable salt thereof varies depending on the type of the health functional food, but is about 0.001 to 10% by weight, preferably 0.1 to 5% by weight.

One embodiment of the present disclosure relates to a method for preventing or treating Parkinson's disease comprising administering to a subject in need thereof an effective amount of a compound represented by the following Chemical Formula I or a pharmaceutically acceptable salt thereof:

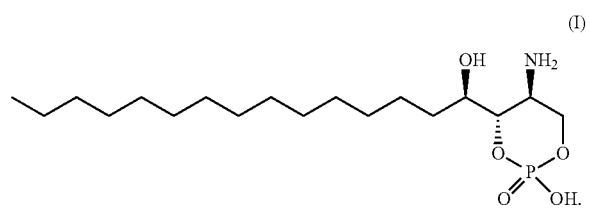

(I)

One embodiment of the present disclosure relates to a use of a compound represented by the following Chemical Formula I or a pharmaceutically acceptable salt thereof for preventing or treating Parkinson's disease:

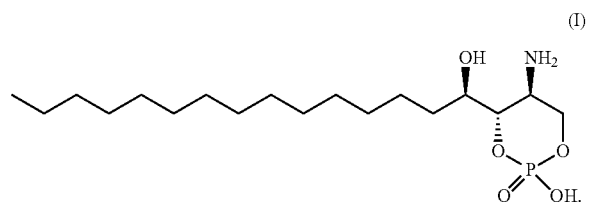

(I)

Advantageous Effects

O-cyclic phytosphingosine-1-phosphate or a pharmaceutically acceptable salt thereof according to the present disclosure can inhibit nerve cell death in a Parkinson's disease cell model induced by treatment with rotenone or MPP$^+$ and increase the expression of tyrosine hydroxylase, an enzyme required for dopamine formation in nerve cells. Accordingly, it can be effectively used in a composition for preventing, treating or improving Parkinson's disease.

BRIEF DESCRIPTION OF FIGURES

FIG. 1 is a graph showing the effect of the concentration of the cP1P drug on the proliferation of the SH-SY5Y human nerve cell line.

FIG. 2 is a graph showing the efficacy of the cP1P drug to inhibit the death of SH-SY5Y nerve cells in the rotenone-treated Parkinson's disease cell model.

FIG. 3 is a graph showing the efficacy of the cP1P drug to inhibit the death of SH-SY5Y nerve cells in the MPP$^+$-treated Parkinson's disease cell model.

FIG. 4 shows the results of measuring the effect of the cP1P drug on the expression of tyrosine hydroxylase (TH) in SH-SY5Y nerve cells by immunohistochemical method and Western blot method.

BEST MODE

Hereinafter, examples are presented to help the understanding of the present invention. However, the following examples are only provided for easier understanding of the present invention, and the present invention is not limited to the following examples.

Example 1: Effects of cP1P Drug on Proliferation of Dopaminergic Human Nerve Cells (SH-SY5Y)

The SH-SY5Y human nerve cell line purchased from ATCC was used as a nerve cell line to evaluate the effect of the cP1P drug on the proliferation of dopaminergic human nerve cells. Dulbeco's Modified Eagle's Media/high glucose (with 10% FBS, 0.5% P/S) was used as a medium for culturing nerve cells, and the nerve cells were cultured at 37° C. in 5% $CO_2$ incubator.

In order to observe the effect of cP1P drug on the proliferation of the dopaminergic human nerve cells, SH-SY5Y cells were treated with cP1P drug at concentrations of 10 nM, 100 nM and 1000 nM, respectively, and cultured for 48 hours. MTT assay (Molecular Probes) was performed according to the manufacturer's method to measure the cell proliferation rate.

The results are shown in FIG. 1.

As shown in FIG. 1, the effect on the proliferation of SH-SY5Y cells appeared even at a low concentration of 10 nM of the cP1P drug. The effect on the nerve cell proliferation was highest when the concentration of the cP1P drug was 100 nM.

Example 2: Effects of cP1P Drug in Rotenone-Treated Parkinson's Disease Cell Model Rotenone is a substance widely used in cell models to induce Parkinson's disease. It is well known that when a nerve cell is treated with rotenone, mitochondrial function is destroyed, and oxidative stress is induced to cause death of the nerve cell.

The SH-SY5Y nerve cell culture medium was treated with cP1P drug at concentrations of 100 nM and 1000 nM, respectively, and cultured for 24 hours. Then, rotenone (Sigma) was dissolved in DMSO, diluted to a final concentration of 2 μM, and added to the SH-SY5Y nerve cell culture medium. The SH-SY5Y nerve cells were cultured for an additional 24 hours. SH-SY5Y nerve cells were obtained and cultured in the same manner as in Example 1.

Necrotic cell death was measured for the cultured SH-SY5Y nerve cells using a lactate dehydrogenase (LDH) detection kit (BioVision).

For comparison, the necrotic cell death was also measured for the control group that was treated only with DMSO without cP1P drug and rotenone, and the control group that was treated only with diluted rotenone solution without cP1P drug. In addition, the necrotic cell death was measured for the treatment of the nerve cells with the cP1P drug at concentrations of 100 nM and 1000 nM, respectively.

The results are shown in FIG. 2.

As shown in FIG. 2, in the control group treated only with rotenone, the degree of nerve cell death was high enough to exceed 30%. However, when the cP1P drug was first treated, the nerve cell death was inhibited to the level equivalent to that of DMSO treatment without rotenone.

In addition, as shown in FIG. 2, the treatment of the cP1P drug reduced the degree of cell death compared to the control group treated only with DMSO. This result appears to be because the treatment with the cP1P drug enhances the proliferation of SH-SY5Y nerve cells. From these results, it can be seen that the cP1P drug is useful as a therapeutic agent for Parkinson's disease.

Example 3: Effects of cP1P Drug in $MPP^+$-Treated Parkinson's Disease Cell Model To prepare a Parkinson's disease cell model by inducing oxidative stress with $MPP^+$ (1-methyl-4-phenylpyridinium iodide, Sigma), $MPP^+$ was dissolved in a phosphate buffer solution, diluted to a final concentration of 3 mM, and added to a nerve cell culture medium. To confirm the efficacy of the cP1P drug in the $MPP^+$ environment, SH-SY5Y cells were pretreated with cP1P drug at concentrations of 10 nM, 100 nM, and 1000 nM, respectively, for 1 hour, and then exposed to oxidative stress by treatment with 3 mM $MPP^+$ for 24 hours. The efficacy of the cP1P drug on the survival of SH-SY5Y cells after 24 hours of exposure to oxidative stress was determined by MTT assay.

The results are shown in FIG. 3.

As shown in FIG. 3, when the SH-SY5Y cell line was treated with $MPP^+$ 3 mM, the nerve cells were killed. However, when the cell line was pretreated with the cP1P drug, the nerve cell death was significantly reduced. In particular, the nerve cell death was significantly reduced when the cP1P drug was treated at a concentration of 100 nM. From these results, it can be seen that the cP1P drug is useful as a therapeutic agent for Parkinson's disease.

Example 4: Effects of cP1P Drug on the Expression of Tyrosine Hydroxylase (TH) Required for Dopamine Formation in Nerve Cells Tyrosine hydroxylase (TH) is an enzyme that converts amino acid tyrosine into L-DOPA, a precursor of dopamine, and plays an important role in the formation of dopamine in nerve cells.

In order to confirm the efficacy of the cP1P drug on TH expression in SH-SY5Y nerve cells, SH-SY5Y nerve cell culture was treated with the cP1P drug at concentrations of 10 nM and 100 nM, respectively. TH expression was determined by immunohistochemistry and western blot after 24 hours.

The results are shown in FIG. 4.

As shown in FIG. 4, the expression of the TH enzyme was increased when the cP1P drug was treated at concentrations of 10 nM and 100 nM. These results show that the cP1P drug can be used as a therapeutic agent for Parkinson's disease caused by the death of dopaminergic nerve cells.

The invention claimed is:

1. A method for treating Parkinson's disease in a subject in need thereof, comprising administering to the subject an effective amount of a compound of the following Chemical Formula I or a pharmaceutically acceptable salt thereof:

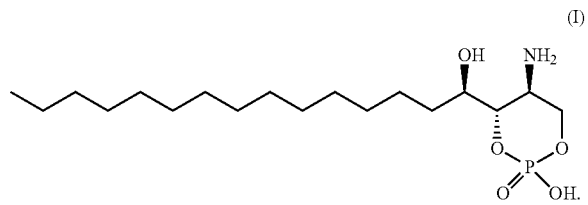

(I)

2. The method according to claim 1, wherein administering the compound of the Chemical Formula I or a pharmaceutically acceptable salt thereof to the subject increases expression of tyrosine hydroxylase in the subject.

3. The method according to claim 1, wherein the pharmaceutically acceptable salt is hydrochloride salt.

4. A method for increasing expression of tyrosine hydroxylase in a subject in need thereof, comprising administering to the subject a compound of the following Chemical Formula I or a pharmaceutically acceptable salt thereof:

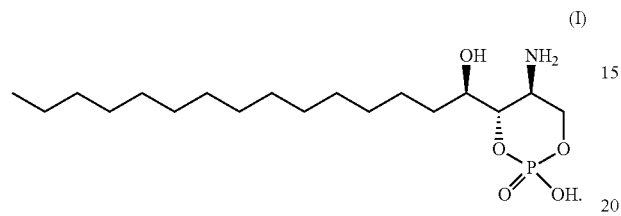

5. The method according to claim 4, wherein the subject has Parkinson's disease.

6. The method according to claim 4, wherein the compound of Chemical Formula I or a pharmaceutically acceptable salt thereof is in a form of a pharmaceutical composition, food composition, or a dietary supplement.

* * * * *